United States Patent
Stahl et al.

(10) Patent No.: US 6,467,905 B1
(45) Date of Patent: Oct. 22, 2002

(54) ACQUIRED PENDULAR NYSTAGMUS TREATMENT DEVICE

(76) Inventors: John S. Stahl, 3304 Chalfant Rd., Shaker Heights, OH (US) 44120; Mark J. Lehmkuhle, 112 S. University St. Apt. B, Salt Lake City, UT (US) 84102; Kelvin Wu, 1700 15th Ave. #207, Seattle, WA (US) 98122; Bennett Curtis Burke, 1815 William Howard Taft Rd., #208, Cincinnati, OH (US) 45206

( * ) Notice: Subject to any disclaimer, the term of this patent is extended or adjusted under 35 U.S.C. 154(b) by 0 days.

(21) Appl. No.: 09/806,064

(22) PCT Filed: Sep. 22, 1999

(86) PCT No.: PCT/US99/21763

§ 371 (c)(1), (2), (4) Date: Oct. 9, 2001

(87) PCT Pub. No.: WO00/18287

PCT Pub. Date: Apr. 6, 2000

Related U.S. Application Data

(60) Provisional application No. 60/101,872, filed on Sep. 25, 1998.

(51) Int. Cl.[7] .................................................. A61B 3/08
(52) U.S. Cl. ........................................ 351/202; 351/203
(58) Field of Search ................................ 351/202, 203, 351/208, 209, 210, 211, 216, 246, 175, 158, 159; 359/554, 557

(56) References Cited

U.S. PATENT DOCUMENTS

| | | | |
|---|---|---|---|
| 4,815,839 A | | 3/1989 | Waldorf |
| 5,002,384 A | | 3/1991 | Trachtman |
| 6,099,124 A | * | 8/2000 | Hidaji .......................... 351/202 |

* cited by examiner

*Primary Examiner*—George Manuel
(74) *Attorney, Agent, or Firm*—Fay, Sharpe, Fagan, Minnich & McKee, LLP

(57) ABSTRACT

A device (10) for treating eye movement disorders is described. The device is wearable, and utilizes servo controlled prisms to treat disorders of ocular mobility in non-invasive and non-pharmacologic manner. Probe (20) comprises an eye movement sensor. The device (10) oscillates the image of the world as perceived by a patient in lock step with pathological nystagmus to negate its deleterious effects. Furthermore, the subject treatment device negates only abnormal eye movement. Voluntary, and normal reflex eye movements required for normal vision do not affect operation of the device. In addition to acquired pendular nystagmus (APN), the device is potentially usable to treat non-sinusoidal ocular oscillations (e.g., jerk nystagmus), strabismus, vestibular insufficiency, and other ocular mobility disorders. A corresponding method for treating APN and other eye movement disorders is also described.

19 Claims, 5 Drawing Sheets

ACQUIRED PENDULAR NYSTAGMUS TREATMENT DEVICE

CROSS-REFERENCE TO RELATED APPLICATION

This application claims priority from U.S. Provisional Application Serial No. 60/101,872 filed Sep. 25, 1998, which application is hereby expressly incorporated by reference herein.

REFERENCE TO FEDERALLY SPONSORED FUNDING

Research for the technology described and claimed herein was at least partially funded by National Institute of Health grant EY-00356 (National Eye Institute).

BACKGROUND OF THE INVENTION

Acquired, involuntary sinusoidal oscillation of the eyes in human patients, commonly referred to as acquired pendular nystagmus (APN), produces an illusion to the patient that his/her surroundings are in motion (oscillopsia) and degrades clarity of vision. Although the exact mechanism of APN is not well understood, it is a neurologic disorder that is often secondary to multiple sclerosis.

Typically, the eyes of a patient suffering from APN will oscillate at a frequency of between 2 and 7 hertz, with amplitudes as high as eight degrees. Consequently, APN is a debilitating disease that prevents people from reading books, watching television, driving, and otherwise participating in everyday activities.

Heretofore, APN has been treated with drugs and/or special spectacles/contact lenses. These prior treatments have been found to be ineffective or suboptimal. A large number of drugs have been reported to treat APN, but efficacy is variable, often incomplete, and some patients fail to respond to all agents. Many patients that do respond to APN drugs have not been able to tolerate the medication on a daily basis due to sedation or ataxia. Other treatment strategies, including weakening selected extraocular muscles with botulinum toxin or using spectacle/contact lens combinations to optically attenuate the visual consequences of APN have proved to be impractical and have failed to gain wide patient acceptance, A main disadvantage of existing surgical and optical APN treatments is that they also impair normal reflex and voluntary eye movements as much as they reduce pathological nystagmus. For example, when treating APN with a spectacle/contact lens combination, the vestibulo-ocular reflex is nullified and, thus, any patient head movements generate oscillopsia.

In light of the foregoing, a need has been identified for a non-surgical non-pharmacologic treatment for APN that reduces oscillopsia and improves acuity, with few or minimal adverse effects. Particularly, a need has been found for a convenient and effective APN treatment device that is wearable by a patient to negate the deleterious effects of APN.

SUMMARY OF THE INVENTION

In accordance with the present invention, a novel and non-obvious non-invasive acquired pendular nystagmus treatment device is provided.

In accordance with another aspect of the present invention, a novel and non-obvious method for treating acquired pendular nystagmus is provided that utilizes a specially designed non-invasive device.

In accordance with still another aspect of the present invention an apparatus for treating acquired pendular nystagmus associated with an eye of a patient is provided. The apparatus includes a sensor for tracking oscillating movement of the eye in at least one plane and outputting an eye movement signal that varies with the oscillating eye movement. An optic assembly is adapted for operative placement relative to the eye of the patient and for translating an image perceived by a patient with his/her eye in the at least one plane in correspondence with the oscillating eye movement. An optic assembly control circuit is operatively connected between the sensor and the optic assembly. The control circuit is adapted for receiving the eye movement signal and controlling the optic assembly in response to the eye movement signal to translate the image perceived by the patient in a manner that corresponds with the oscillating eye movement.

In accordance with still another aspect of the present invention, a method of treating an eye movement disorder associated with an eye of a patient includes tracking involuntary movements of the eye in at least one plane. The method further includes optically translating an image perceived by the patient with the eye in the at least one plane and in correspondence with the tracked involuntary movements of the eye in the at least one plane.

In accordance with yet another aspect of the present invention, an apparatus for treating an involuntary eye movement disorder of a patient is provided. The apparatus includes a sensor for tracking involuntary movement of the patient's eye in at least one plane and outputting a control signal that varies with the tracked involuntary eye movement. The apparatus also includes an optic assembly adapted for operative placement relative to the patient's eye and for translating an image perceived by the patient in the at least one plane in correspondence with the involuntary eye movement. An optic assembly control circuit is provided and operatively connected between the sensor and the optic assembly. The control circuit is adapted for receiving the control signal and controlling the optic assembly in response to the control signal to translate the image perceived by the patient in a manner that corresponds with the involuntary eye movement.

One advantage of the present invention resides in the provision of a non-invasive device for treating acquired pendular nystagmus without surgery or drugs.

Another advantage of the present invention is found in the provision of a method for treating acquired pendular nystagmus using a specially designed device.

A further advantage of the present invention is the provision of a method and apparatus for treating acquired pendular nystagmus wherein normal reflex and voluntary eye movements are not impaired.

Another advantage of the present invention resides in the provision of a device for treating acquired pendular nystagmus that is wearable by the patient.

Still other benefits and advantages of the present invention will become apparent to those of ordinary skill in the art to which the invention pertains upon reading and understanding the following specification.

BRIEF DESCRIPTION OF THE DRAWINGS

The invention takes form from various components and arrangements of components, and in various steps and arrangements of steps, preferred embodiments of which are illustrated in the accompanying drawings that form a part hereof and wherein.

DETAILED DESCRIPTION OF PREFERRED EMBODIMENTS

Figure 1:
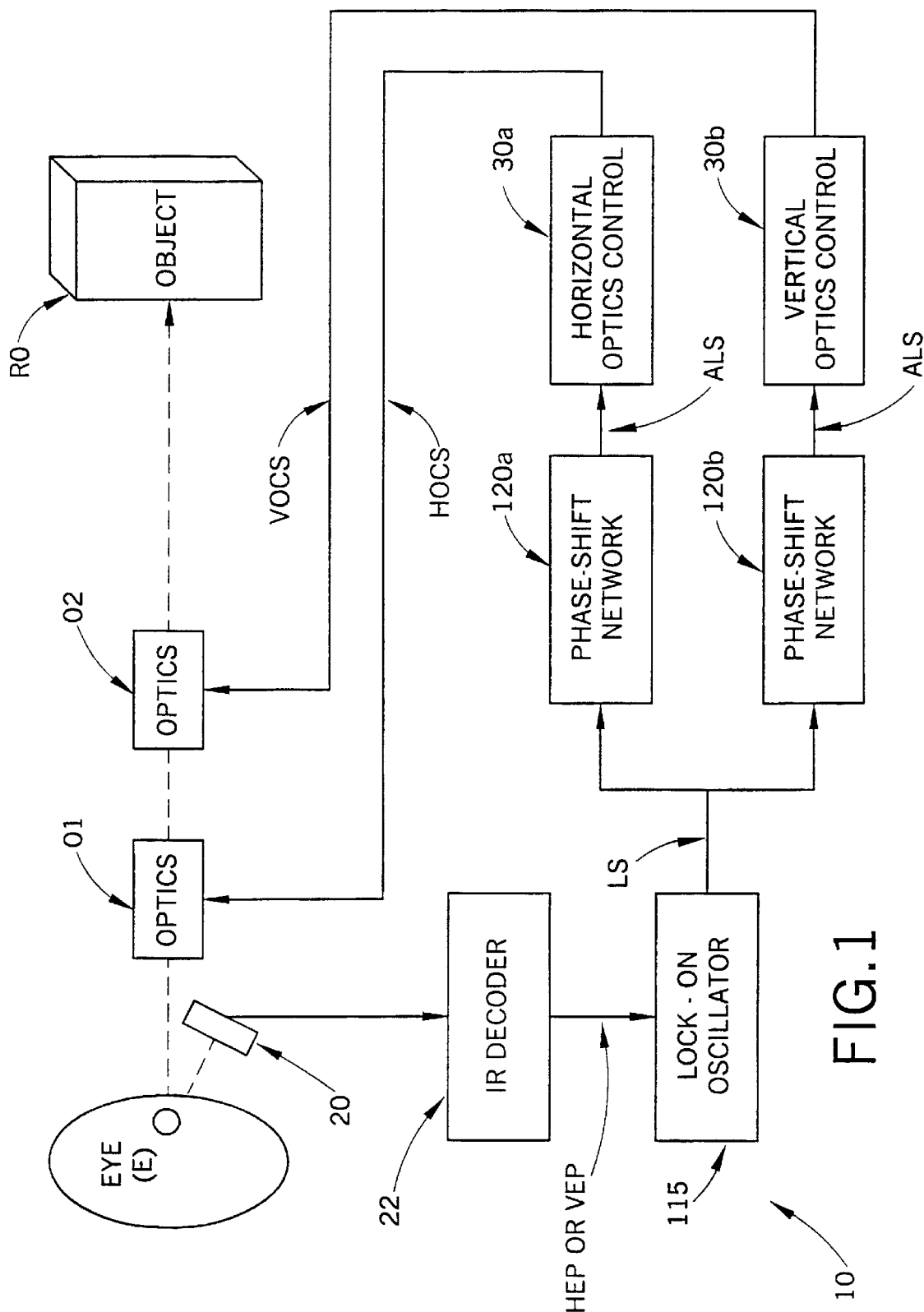
FIG. 1 is a simplified diagrammatic illustration of an acquired pendular nystagmus treatment device formed in accordance with the present invention.

Referring now to the FIGURES, wherein the showings are for purposes of describing preferred embodiments of the invention and not for purposes of limiting same, FIG. 1 illustrates an acquired pendular nystagmus (APN) treatment device 10 formed in accordance with the present invention. The illustrated device 10 is adapted for treating APN or other eye movement disorders in one eye E, but those of ordinary skill in the art will recognize that an identical device can be used to treat APN or other disorders in a second eye of a patient. In general, first and second optic assemblies O1,O2 are placed in an operative position relative to the eye E and used to compensate for horizontal and vertical ocular oscillations, respectively, so that a regarded object RO is viewed more acutely. That is to say, the first and second optic assemblies O1,O2 are modulated to oscillate the patient's image or perception of the regarded object RO in step with the involuntary horizontal and/or vertical ocular oscillations to cancel the motion of the regarded object RO that would otherwise be perceived by the patient.

An eye movement sensor, such as an infrared (IR) reflectance system including an IR probe 20 and an IR decoder 22, preferably battery powered for portability and mounted in a goggle or spectacle assembly with the optics O1,O2, is used to track involuntary oscillation of the patient's eye E. A suitable IR reflectance system is commercially available from Microguide, Inc., Downers Grove, Ill. (Series 1000). Based upon the horizontal and vertical positions of the eye E as detected by the IR probe 10, the IR decoder 22 derives and outputs a horizontal eye position signal HEP and a vertical eye position VEP signal, indicative of and proportional to the horizontal and vertical positions of the eye E, respectively. Depending upon the spatial characteristics of the patient's involuntary ocular oscillations, one channel (vertical or horizontal) will carry a stronger, higher signal-to-noise ratio oscillation signal. In practice, the IR decoder 22 is set to output the strongest one of the eye position signals HEP,VEP for use in controlling the optic assemblies O1,O2.

The selected one of the eye position signals HEP,VEP is output from the IR decoder 22 to a lock-on oscillator circuit 115, such as a phase-locked loop (PLL) circuit or the like, that locks onto the input signal HEP,VEP and outputs a clean, unmodulated, sinusoidal lock signal LS that bears a constant phase relationship to the original vertical and horizontal ocular oscillations. As is described below, the single lock signal LS, based upon the strongest of the horizontal and vertical eye position signals HEP,VEP, is used to drive both the horizontal and vertical optics control circuits 30a,30b. In practice, only the strongest eye position signal of the horizontal and vertical eye position signals need be tracked by the IR reflectance system, because horizontal and vertical components of the nystagmus are almost always phase-locked.

The lock signal LS is input to horizontal and vertical phase-shift networks 120a,120b that output phase-adjusted lock signals ALS. The horizontal and vertical phase-shift networks 120a,120b are preferably provided as part of horizontal and vertical optic control circuits 30a,30b, respectively. The horizontal and vertical optic control circuits 30a,30b respectively derive and output horizontal and vertical optic control signals HOCS,VOCS that control the speed and direction of rotation of first and second Risley prisms RP1,RP2 (FIG. 3) (or modulation other optics) in the first and second optic assemblies O1,O2 to translate the patient's perception of the regarded object RO horizontally and vertically, respectively, at a speed and direction that match the oscillations of the eye E. This, then, attenuates the visual consequences of the patient's ocular oscillations due to APN or other disorder.

The optic assemblies O1,O2, which are preferably consolidated into a single assembly for more convenient wearing and use, are identically constructed, but oriented differently to produce horizontal and vertical translation of the regarded object, respectively. The optic assemblies are described in full detail below with reference to FIGS. 2A and 2B wherein the construction of the first optic assembly O1 is shown as an example. In general, each optic assembly O1,O2 comprises a motor-driven Risley prism configuration, i.e., a pair of circular wedge prism that, when counter-rotated about an optical axis, translate the regarded object RO in a single plane as perceived by the patient. The optic assemblies O1,O2 for each eye E of a patient are preferably provided in the form of goggles, eye-glasses, or a headset apparatus that is portable and wearable by a user. Alternatively, the optic assemblies can be incorporated into a larger viewing apparatus that is placed near a patient's television viewing or reading area, or in any other permanent or semi-permanent mounting location to facilitate viewing television, reading, or other specific activities. Obviously, the various components of the optic assemblies are preferably manufactured as small and as light as possible (e.g., from light-weight metal such as aluminum or from polymeric materials) to improve portability and wearability. As an alternative to motor-driven prisms, the optic assemblies O1,O2 can each utilize a variable power prism, such as VARI-ANGLE™ prisms commercially available from Canon, Inc., or any other suitable optics that are able to be modulated to translate an image of the regarded object RO as perceived by a patient through his/her eye E.

Figure 2:
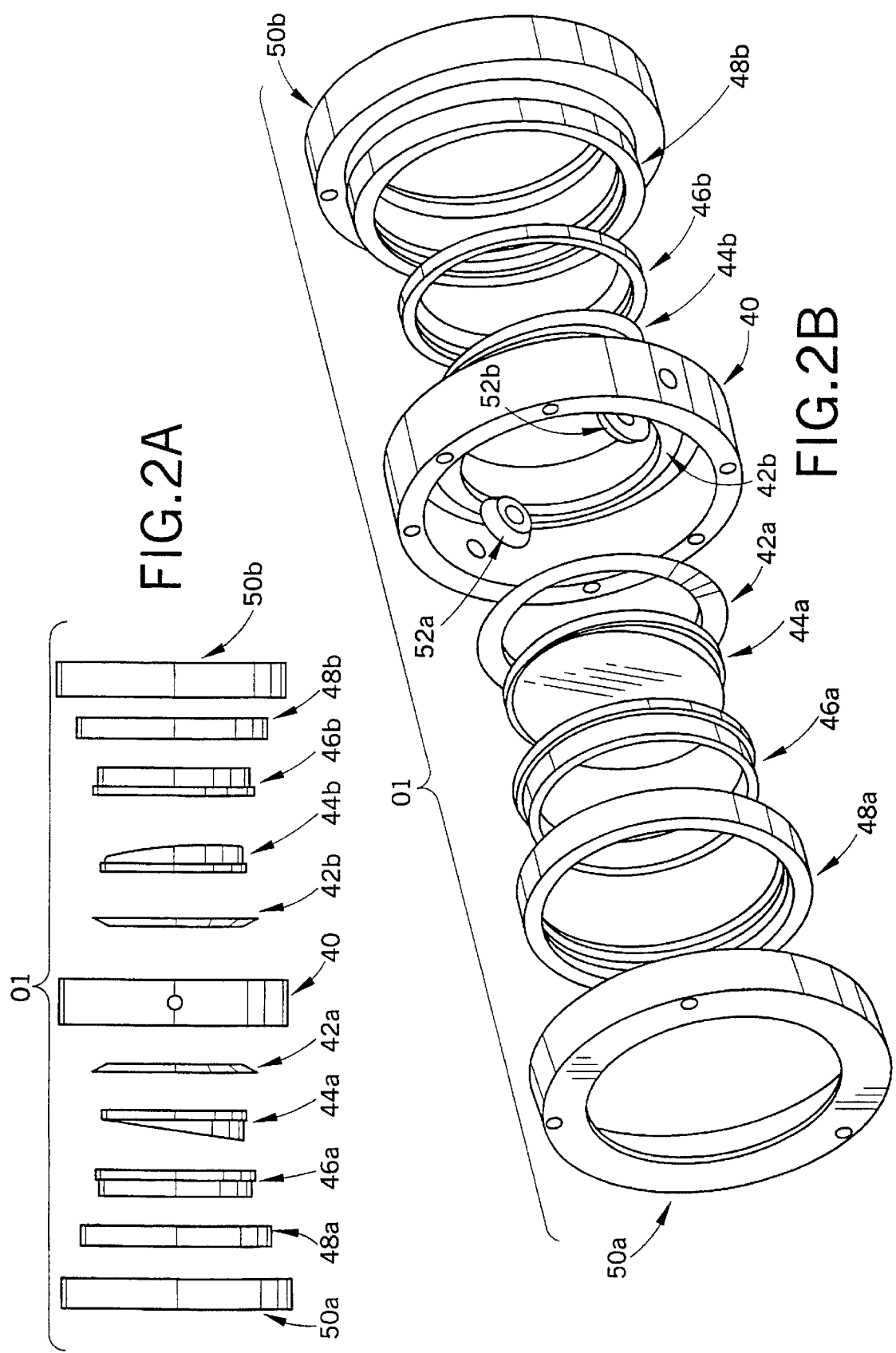
FIG. 2A is an exploded side view of an optic assembly formed in accordance with the present invention and adapted for translating an image on an axis in the frontal plane of a patient.
FIG. 2B is an exploded perspective view of the optic assembly of FIG. 2A.

Referring now particularly to FIGS. 2A and 2B, the optic assembly O1 comprises a gear housing 40 and first and second beveled spur gears 42a,42b. First and second prisms 44a,44b are secured to rotate with first and second inner races 46a,46b and also with the first and second spur gears 42a,42b, respectively. The first and second inner races 46a,46b are rotatably received in first and second nylon bushings 48a,48b, and the bushings are, in turn, seated in first and second outer casings 50a,50b, respectively. The outer casings 50a,50b, with the bushings/races/prisms/gears seated therein are secured to the central gear housing 40 with fasteners or the like so that the first and second beveled gears 42a,42b are placed in spaced-apart, opposed facing relation.

The gear housing 40 rotatably supports first and second pinion gears 52a,52b that are engaged with both the first and second bevel gears 42a,42b. As is described in full detail below, at least one of the pinion gears 52a,52b is driven by a stepper motor SM1 (FIG. 3) to counter rotate the beveled gears 42a,42b and, consequently, counter-rotate the prisms 44a,44b to translate a regarded object RO as perceived by a patient through his/her eye E. The prisms 44a,44b, together, form a Risley prism. Thus, the pair of prisms 44a,44b in the first optic assembly O1 are collectively referred to herein as the first or horizontal Risley prism RP1, and the pair of prisms 44a,44b in the second optic assembly O2 are collectively referred to herein as the second or vertical Risley prism RP2.

Although it is not intended that the invention be limited to any particular prisms 44a,44b, a preferred embodiment employs ten diopter plastic prisms for both the first and second prisms 44a,44b, each defined to provide 6° of nominal deviation. Also, the prisms 44a,44b are arranged in the optic assemblies O1,O2 to be 180° out-of-phase in the neutral position, i.e., the orientation in which the prisms 44a,44b do not deflect/translate the image of the regarded object RO as perceived through the eye E of the patient. As constructed in one embodiment, a full rotation of the pinion gears 52a,52b produces 45° of counter-rotation in each of the two bevel gears 42a,42b and attached prisms 44a,44b. Thus, rotation of the pinion gears one full rotation in either direction will yield relative prism positions in the range of 90°–270 , i.e., 90° either side of the neutral 180° position. Given each wedge prism 44a,44b is selected to generate a deflection/translation of 6° , this configuration will deflect/translate the image of the regarded object RO over a range spanning ±8.5° (2*6*cos45) as perceived by the patient through his/her eye E.

Figure 3:
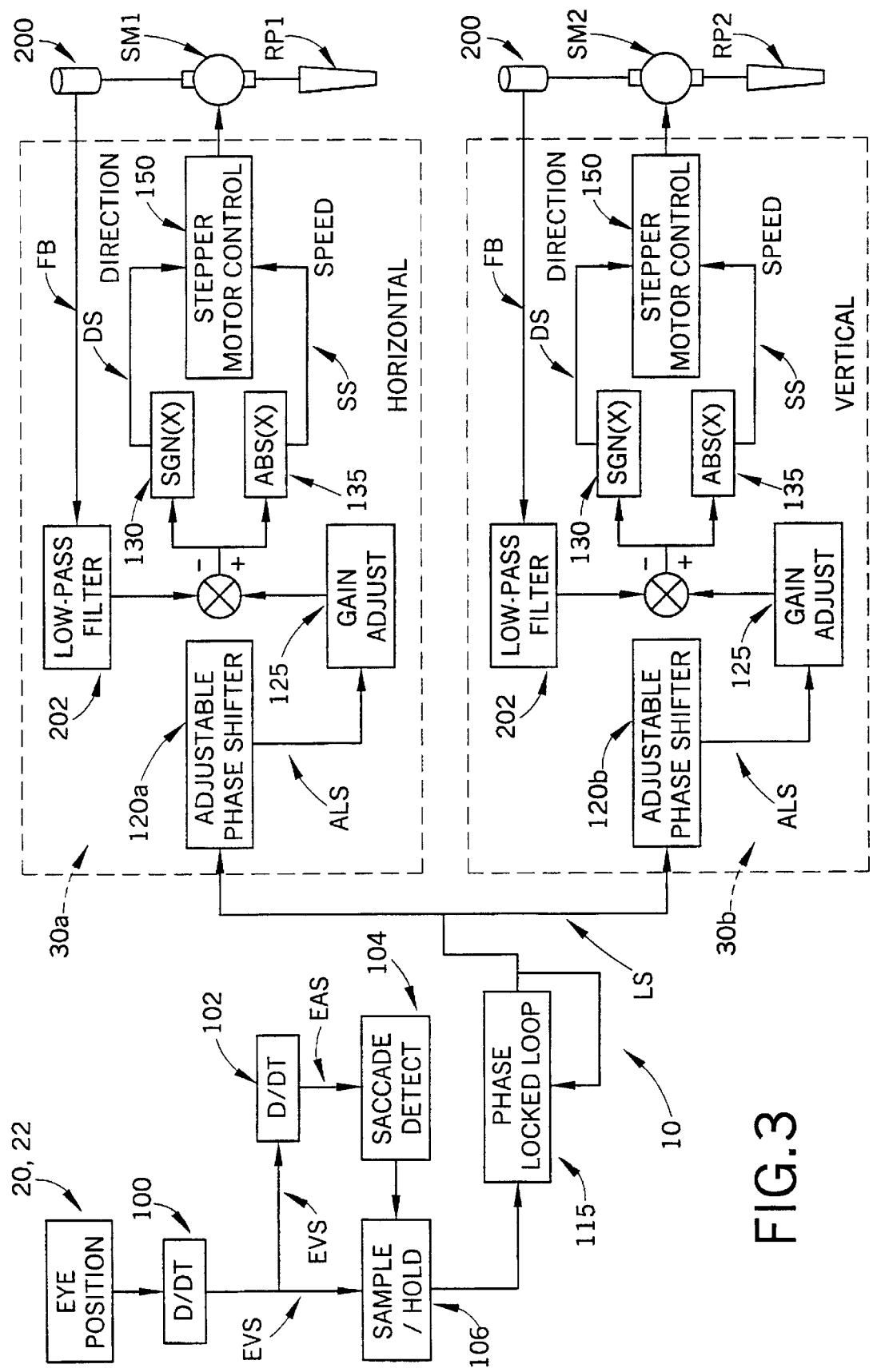
FIG. 3 is a block diagram illustrating an acquired pendular nystagmus treatment device adapted for controlling both vertical and horizontal sinusoidal oscillations in one eye of a patient (of course an identical system could be employed for a second eye of the patient)

Turning now to FIG. 3, the acquired pendular nystagmus treatment device 10 formed in accordance with the present invention is illustrated in further detail. The IR reflectance system 20,22 or other eye sensor tracks vertical and horizontal movement of the patient's eye E (FIG. 1) . The strongest one of these horizontal and vertical eye position signals HEP,VEP is input to a differentiator 100 such as operational amplifier or like means adapted to differentiate the eye position signal and derive a velocity of eye movement. The differentiator 100 outputs either a horizontal or vertical eye velocity signal EVS indicative of horizontal or vertical eye velocity, respectively, depending upon whether the horizontal or vertical eye position signal is supplied thereto. Those of ordinary skill in the art will recognize that changes in eye movement direction can also be determined from the eye velocity signal EVS by changes in the "sign" thereof.

The eye velocity signal EVS ultimately controls the optic assemblies O1,O2. However, in order to reduce the likelihood that voluntary gaze shifts (saccades) will disrupt the proper function of the optic control circuits 30a,30b, changes in the eye velocity signal EVS corresponding to saccades are detected and blocked by a saccade detect circuit 104 and a sample/hold circuit 106. In particular, a second differentiator 102 receives the eye velocity signal EVS and converts same into an eye acceleration signal EAS indicative of acceleration of the movement of the eye E. This eye acceleration signal EAS is input to the saccade detection circuit 104 that monitors the eye acceleration signal and controls the sample/hold circuit 106 based thereon.

Given that even small saccades involve very high acceleration in movement of the eye E and corresponding spikes in the eye acceleration signal EAS, the saccade detection circuit 104 maintains the sample/hold circuit 106 in a "pass-through" mode, wherein the circuit 106 passes the eye velocity signal EVS to the phase-locked loop circuit 115, when the eye acceleration signal EAS is below a select threshold indicative of saccades. On the other hand, if the saccade detect circuit 104 detects an increase in the eye acceleration signal EAS above the select saccades threshold, it triggers the sample/hold circuit 106 into a "hold" mode wherein further changes in the eye velocity signal EVS are blocked from reaching the phaselocked loop 115. In its "hold" mode, the sample/hold circuit 106 maintains an output to the phase-locked loop circuit 115 that is equal to the value of the eye velocity signal EVS existing just prior to the detection of saccades by the circuit 104. When the saccade detect circuit 104 detects a drop in the eye acceleration signal EAS below the saccades threshold, it again places the sample/hold circuit 106 in its "pass-through" mode. Thus, spikes in the eye velocity signal EVS due to saccades are prevented from even reaching the phase-locked loop circuitry 115 and having any effect on modulation of the optic assemblies O1,O2.

The phase-locked loop (PLL) circuit 115, itself, provides several benefits. The phase-locked loop circuit 115 is configured to lock to the eye velocity signal EVS only when the signal has a frequency in the approximate range of 2–10 Hertz (Hz), with an acquisition time of 2–3 cycles, and outputs a lock signal LS that varies with the locked eye velocity signal. Accordingly, the phase-locked loop circuit 115 has low-pass characteristics that further guarantee momentary transients in the eye velocity signal (e.g., from saccades) will not be tracked. Likewise, slow eye movements related to the vestibulo-ocular reflex or smooth pursuit have essentially no effect on the lock signal LS output from the phase-locked loop circuit 115. The lock signal LS output by the phase-locked loop circuit 115 is split and input to both the horizontal optic control circuit 30a and the vertical optic control circuit 30b.

The horizontal and vertical optic control circuits 30a,30b are preferably structured and operate identically. Of course, the first and second optic assemblies O1,O2 controlled thereby are oriented differently to produce horizontal and vertical translation, respectively, of the regarded object RO as perceived by the patient through his/her eye E. Accordingly, for ease of understanding the present invention, only the horizontal optic control circuit 30a is described in full detail.

The lock signal LS is input to an adjustable phase shifter circuit 120a which, by shifting the phase of the lock signal LS, causes the phase of the prisms 44a,44b of the horizontal optic assembly O1 to match exactly the phase of the horizontal ocular oscillation. The adjustable phase shifter circuit 120a outputs an adjusted lock signal ALS to a gain adjust circuit 125 that causes the amplitude of horizontal image translation as perceived by the patient through the horizontal prism assembly O1 to match exactly the amplitude of horizontal ocular oscillation.

The adjusted lock signal ALS is output from the gain adjust circuit 125 and fed to both a sign detection circuit 130 and a magnitude or absolute value circuit 135 that respectively derive and output a direction signal DS and a speed signal SS. The direction signal depends upon the "sign," i.e., (+) or (−), of the adjusted lock signal ALS, and the speed signal depends upon the magnitude of the adjusted lock signal ALS. The direction and speed signals DS,SS are fed to a stepper motor control circuit 150 that controls the first stepper motor SM1 in accordance therewith. One suitable stepper motor SM1 is commercially available Oriental Motors USA Corporation, Torrance, California as model number PK243-01BA, and a suitable stepper motor control circuit 150 for the motor SM1 is a model number UDK2109A controller module commercially available from the same source. As noted above, the stepper motor SMI modulates the prisms 44a,44b in the optic assembly O1.

The subject treatment device 10 also preferably comprises a prism position sensor 200, such as a potentiometer operatively coupled to the output shaft of the stepper motor SM1, that outputs a feedback signal FB. The prism position feedback signal FB is low-pass filtered and combined with the adjusted lock signal output from the gain adjuster 125. The sensor 200 is adapted and connected to output the feedback signal FB with a positive or negative sign that ensures the optic control circuit 30a will maintain the average prism position centered at the point where angular deflection of the regarded object RO, as perceived by the patient through the optic assembly O1, is nil.

The device 10 has been tested on various patients and found to be effective in reducing oscillopsia and improving acuity in patients suffering from acquired pendular nystagmus. All patients reported a decrease in oscillopsia using the device 10. Averaging across patients, the device 10 increased the percentage of time in which retinal velocity was within ±4°/second from 12.8% to 33.3%. Also, acuities improved in 4 of 5 patients, by an average of 0.18 logMAR units.

Figure 4:
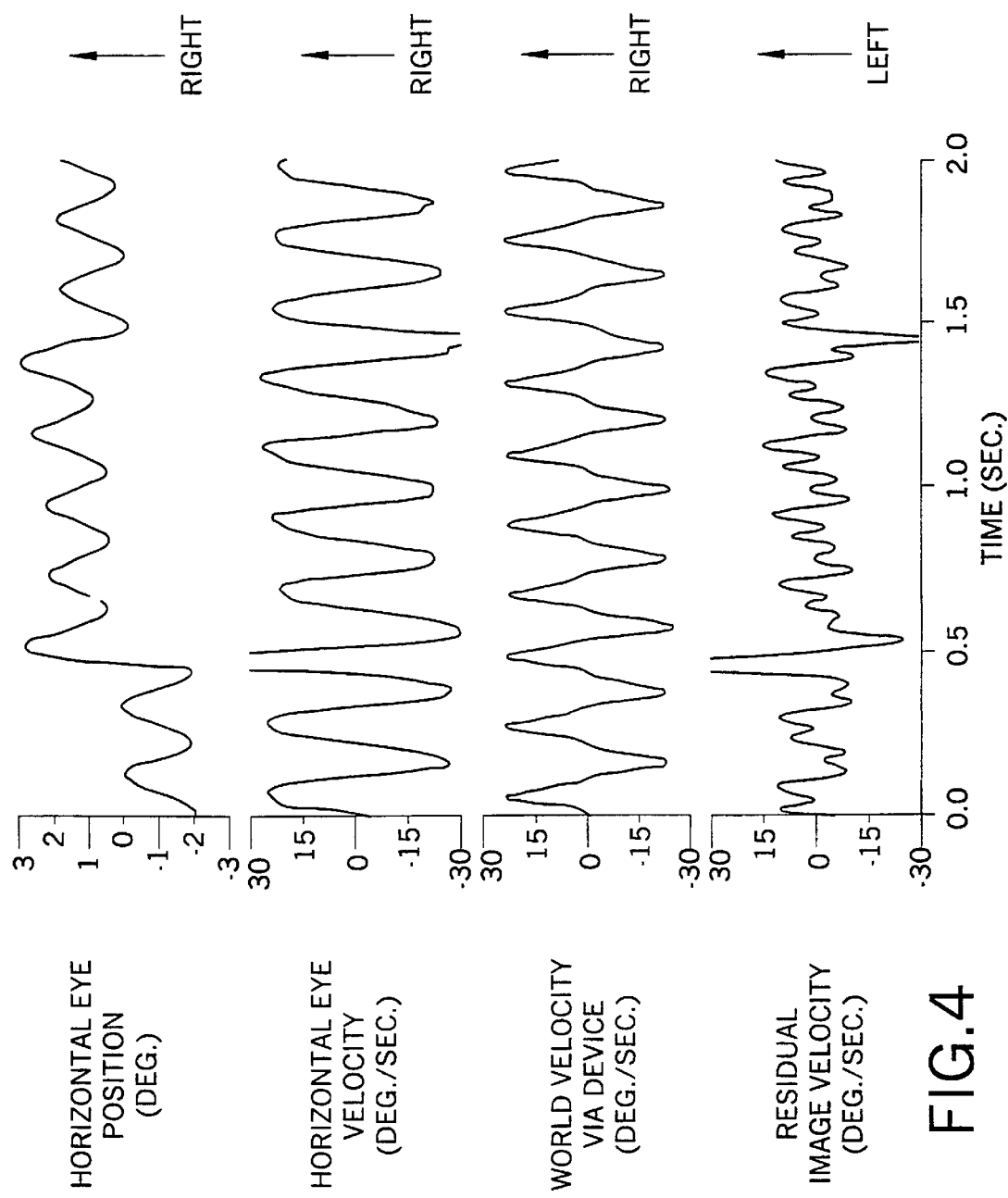
FIG. 4 graphically illustrates a 2-second segment of horizontal ocular oscillations for a patient, and control of the optic assembly based upon the ocular oscillations to minimize residual image velocity experienced by the patient; and, FIG. 5 graphically illustrates a plot of accuracy versus optotype size for a patient when the treatment device of the present invention is "off" and "on".
Figure 5:
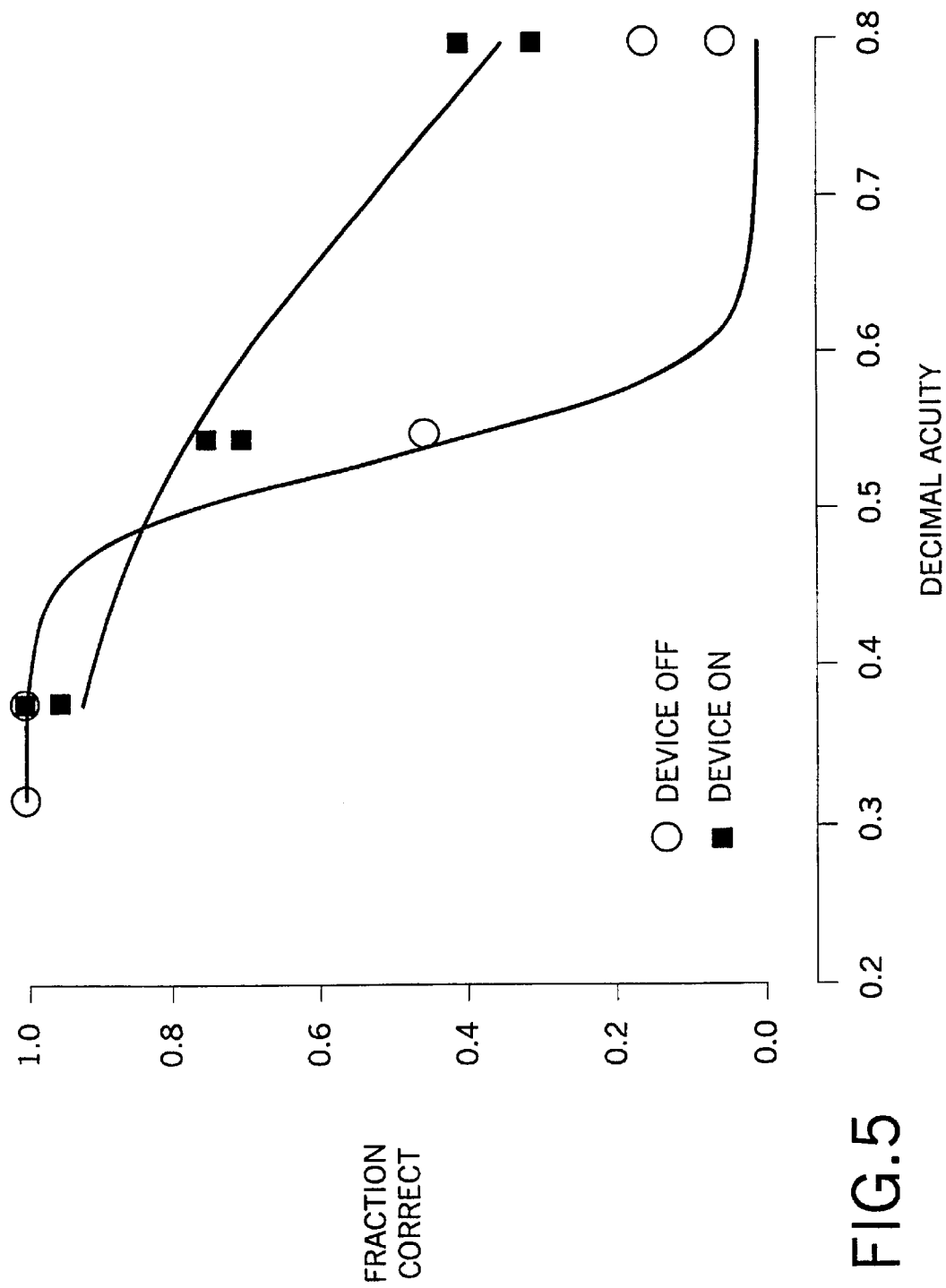

Pertinent testing data for one patient are illustrated in FIGS. 4 and 5. The patient was a woman with multiple sclerosis who had suffered APN for 6 years. She had previously received only little symptomatic relief from multiple treatments, including gabapentin, clonazepam, trihexyphenidyl, baclofen, and amantadine. Her nystagmus was predominantly monocular, nearly perfectly sinusoidal, and essentially purely horizontal, with an average frequency of 4.7 Hz. Position amplitudes varied, tending to increase with fatigue. During her testing, the 0-peak position amplitude averaged 0.7° (velocity amplitude of 21°/second). The patient had not suffered an episode of optic neuritis, and a clinical examination revealed neither relative afferent pupillary defect nor optic disc pallor.

FIG. 4 shows a 2-second segment of her ocular oscillations, recorded with the device 10 in operation. In the absence of the device 10, the patient experienced a retinal slip velocity equal and opposite to her eye velocity. With the device 10 in operation, the patient experienced only a residual image velocity (see the bottom trace of FIG. 4) that was calculated from the difference between eye velocity and angular velocity of the world imparted by the movement of the prism RP1. Comparison of the eye and residual image velocity traces in FIG. 4 reveals how the device 10 reduced peak-to-peak retinal image velocity by more than 50%.

It is important to note that the record indicates two small saccades and, due to the phase-locked loop (PLL) circuit 115, these had no effect on the oscillation of the prism RP1. This is desirable as the device 10 should only counter the involuntary eye oscillations.

The patient noted that her oscillopsia was consistently reduced, and the visual world (i.e., the regarded object RO) appeared clearer when the device 10 was in use. Her acuity was assessed using computer-generated Landolt C optotypes. FIG. 5 plots the fraction of correctly identified optotypes, as a function of optotype size expressed in terms of decimal acuity. The patient's accuracy was uniformly better using the device 10 (the filled square data points) compared to switching the device 10 "off" (the open circle data points). The accuracy data were fit with 3-term sigmoidal curves, and the points at which the fitted curves fell below 50% accuracy determined.

With the device 10 "on," accuracy fell below the 50% criterion at an optotype size of 0.71, versus 0.54 with the device "off." This difference represents a logMAR change of 0.12, or a shift in the 50% accuracy point of better than one line on a logarithmic acuity chart.

Those of ordinary skill in the art will appreciate from the foregoing that a treatment device 10 formed in accordance with the present invention has wider application to treatment of other eye movement disorders.

The device 10 provides a wearable device that utilizes servo-controlled prisms to treat disorders of ocular mobility in a non-invasive and non-pharmacologic manner. Furthermore, a treatment device and/or and method in accordance with the present invention provides a non-pharmacologic treatment for eye movement disorders that selectively negates only the abnormal eye movement. Earlier attempts to improve acuity by servo-mechanical means were not aimed at treatment—instead, these prior attempts nullified all eye movements (not just the nystagmus), and the prior methodology could not have been modified for use as a practical treatment. In contrast, the subject device 10 has been tested and proven effective for practical treatment. In addition to APN, the device 10 could potentially be used to treat non-sinusoidal ocular oscillations (e.g., jerk nystagmus), strabismus, vestibular insufficiency, and other disorders.

Modifications to the device 10 are contemplated and within the scope of the present invention. For example, other eye movement sensors, such as video-based sensors are contemplated. Furthermore, the horizontal and vertical optic assembly control circuits 30a,30b could be implemented using micro-processor based circuitry that would be more robust than the above-described purely analog circuits. As noted above, different optics (such as VARI-ANGLE™ prisms) would be more practical for a wearable device. Furthermore, by coupling the servo-controlled optics to a sensor adapted to sense movement of the patient's head, the device 10 could be used to treat the unpleasant visual consequences of vestibular insufficiency, a common cause of dizziness.

The invention has been described with reference to preferred embodiments. Obviously, modifications and alterations will occur to others upon reading and understanding the preceding specification. It is intended that the invention be construed as including all such modifications and alterations insofar as they are within the scope of the appended claims and equivalents thereto.

Having thus described the preferred embodiments, what is claimed is:

1. An apparatus for treating acquired pendular nystagmus associated with an eye of a patient, said apparatus comprising:

a sensor for tracking oscillating movement of said eye in at least one plane and outputting an eye movement signal that varies with said oscillating eye movement;

an optic assembly adapted for operative placement relative to said eye of said patient and for translating an image perceived by a patient with said eye in said at least one plane in correspondence with said oscillating eye movement; and, an optic assembly control circuit operatively connected between said sensor and said optic assembly, said optic assembly control circuit adapted for receiving said eye movement signal and controlling said optic assembly in response to said eye movement signal to translate said image perceived by said patient in said at least one plane in a manner that corresponds with said oscillating eye movement.

2. The apparatus as set forth in claim 1, wherein said sensor comprises an infrared reflectance system including:
an infrared probe; and,
an infrared decoder operatively connected to said infrared probe and adapted for deriving a position of the eye and outputting an eye position signal, said apparatus further comprising:
means adapted for receiving said eye position signal, deriving a velocity of said eye movement based upon the eye position signal, and outputting an eye velocity signal to said optic assembly control circuit that varies based upon the derived velocity of the eye.

3. The apparatus as set forth in claim 1, further comprising:
a phase-locked loop circuit operatively connected between said sensor and said optic assembly control circuit, said phase-locked loop circuit adapted to lock to said eye position signal only when said eye position signal has a frequency in a select range, whereby said eye position signal is input to said optic assembly control circuit only when said eye position signal has a frequency in said select range.

4. The apparatus as set forth in claim 3, wherein said select range is 2–10 Hertz.

5. The apparatus as set forth in claim 1, wherein said optic assembly comprises:
at least first and second prisms placed relative to each other to form a Risley prism; and,
a motor operatively connected to at least one of said first and second prisms and with said optic assembly control circuit, said motor adapted for rotating said at least one prism relative to the other of said first and second prisms to translate said image perceived by said patient in said at least one plane in response to a motor control signal output by said optic assembly control circuit.

6. A method of treating an eye movement disorder associated with an eye of a patient, said method comprising:
tracking involuntary movements of the eye in at least one plane;
optically translating an image perceived by the patient with the eye in said at least one plane and in correspondence with said tracked involuntary movements of the eye in said at least one plane.

7. The method of treating an eye movement disorder as set forth in claim 6, wherein said step of optically translating the image perceived by said patient with the eye comprises:
placing at least one prism in an operative position optically between the eye and an object regarded by the eye;
modulating the prism to translate an image of the regarded object, as perceived by said patient through said prism, in said at least one plane.

8. The method of treating an eye movement disorder as set forth in claim 7, wherein said at least one prism is a Risley prism comprising first and second prism elements aligned on an optical axis, whereby said prism is modulated by rotating at least one of said first and second prisms about said optical axis.

9. The method of treating an eye movement disorder as set forth in claim 8, wherein said first and second prisms are adapted for counter-rotation relative to each other about said optical axis, wherein said Risley prism is modulated by counter-rotating said first and second prisms relative to each other.

10. The method of treating an eye movement disorder as set forth in claim 6, wherein said step of tracking eye movements comprises using an infrared tracking device.

11. The method of treating an eye movement disorder as set forth in claim 6, wherein said step of tracking movements of the eye comprises tracking only involuntary sinusoidal movements of the eye and disregarding voluntary movements of the eye.

12. The method of treating an eye movement disorder as set forth in claim 11, wherein said step of tracking only involuntary sinusoidal eye movements comprises tracking only involuntary sinusoidal movements of the eye having a frequency in a select range.

13. The method of treating an eye movement disorder as set forth in claim 12, wherein said select range is 2–10 Hertz.

14. The method of treating an eye movement disorder as set forth in claim 6, wherein said step of tracking movements of the eye in at least one plane comprises tracking movements of the eye in one of a horizontal plane and a vertical plane.

15. An apparatus for treating an involuntary eye movement disorder of a patient, said apparatus comprising:
a sensor for tracking involuntary movement of an eye of a patient in at least one plane and outputting a control signal that varies with said involuntary eye movement;
an optic assembly adapted for operative placement relative to said eye of said patient and for translating an image perceived by a patient with said eye in said at least one plane in correspondence with said involuntary eye movement; and,
an optic assembly control circuit operatively connected between said sensor and said optic assembly, said optic assembly control circuit adapted for receiving said control signal and controlling said optic assembly in response to said control signal to translate said image perceived by said patient in said at least one plane in a manner that corresponds with said involuntary eye movement.

16. The apparatus as set forth in claim 15, wherein said sensor comprises an infrared reflectance system including:
an infrared probe; and,
an infrared decoder operatively connected to said infrared probe and adapted for deriving a position of the eye and outputting an eye position signal as said control signal, said apparatus further comprising:
means adapted for receiving said eye position signal;
means for deriving a velocity of said eye movement based upon the eye position signal; and,
means for outputting an eye velocity signal to said optic assembly control circuit that varies based upon the derived velocity of the eye.

17. The apparatus as set forth in claim 15, further comprising:

a phase-locked loop circuit operatively connected between said sensor and said optic assembly control circuit, said phase-locked loop circuit adapted to lock to said control signal only when said control signal has a frequency in a select range, whereby said control signal is input to said optic assembly control circuit only when said control signal has a frequency in said select range.

18. The apparatus as set forth in claim 17, wherein said select range is 2–10 Hertz.

19. The apparatus as set forth in claim 17, further comprising:

an eye acceleration circuit that outputs an eye acceleration signal indicative of acceleration of said eye movement; and, a sample/hold circuit, intermediate said sensor and said phase-locked loop circuit, for receiving said eye acceleration signal and blocking said control signal from being input to said phase-locked loop circuit when said eye acceleration signal exceeds a select threshold indicative of saccades.

* * * * *